United States Patent
Moore, II et al.

(10) Patent No.: US 11,981,756 B2
(45) Date of Patent: May 14, 2024

(54) TEMPO-CELLULOSE STRUCTURES AND RELATED METHODS

(71) Applicant: The Board of Trustees of the University of Arkansas, Little Rock, AR (US)

(72) Inventors: John P. Moore, II, Fayetteville, AR (US); Jamie Hestekin, Fayetteville, AR (US); Peter Crooks, Little Rock, AR (US); Narsimha Reddy Penthala, Little Rock, AR (US); Shobanbabu Bommagani, Little Rock, AR (US); Soma Shekar Dachavaram, Little Rock, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 232 days.

(21) Appl. No.: 16/634,703

(22) PCT Filed: Jul. 30, 2018

(86) PCT No.: PCT/US2018/044343
§ 371 (c)(1),
(2) Date: Jan. 28, 2020

(87) PCT Pub. No.: WO2019/023702
PCT Pub. Date: Jan. 31, 2019

(65) Prior Publication Data
US 2020/0199256 A1  Jun. 25, 2020

Related U.S. Application Data (60) Provisional application No. 62/538,375, filed on Jul. 28, 2017.

(51) Int. Cl.
*C08B 15/04* (2006.01)
*B65D 65/46* (2006.01)
*B65D 81/18* (2006.01)
*B82Y 30/00* (2011.01)

(52) U.S. Cl.
CPC ............ *C08B 15/04* (2013.01); *B65D 65/466* (2013.01); *B65D 81/18* (2013.01); *B82Y 30/00* (2013.01)

(58) Field of Classification Search
CPC ........ C08B 15/04; B65D 65/466; B65D 81/18
See application file for complete search history.

(56) References Cited

U.S. PATENT DOCUMENTS

| | | | |
|---|---|---|---|
| 6,686,464 B1 | 2/2004 | Harding et al. | |
| 9,328,459 B2 * | 5/2016 | Weerawarna | D21C 9/005 |
| 2002/0098317 A1 | 7/2002 | Jaschinski et al. | |
| 2015/0203594 A1 | 7/2015 | Orelma et al. | |
| 2016/0130056 A1 | 5/2016 | Nishijima et al. | |
| 2016/0153144 A1 | 6/2016 | Hiltunen et al. | |
| 2016/0177512 A1 | 6/2016 | Kawahara et al. | |
| 2018/0066072 A1 * | 3/2018 | Takaichi | D21H 11/18 |

OTHER PUBLICATIONS

Spence et al ("The effec of chemical composition on microfibrillar cellulose films from wood pulps: water interactions and physical properties for packaging applications", Cellulose (2010) 17:835-848) (Year: 2010).*
Bragd et al., Carbohydrate Polymers, 2002, 49, p. 397-406. (Year: 2002).*
International Search Report and Written Opinion corresponding to PCT/US2018/044343, mailed Nov. 19, 2018, 11 pages.
Yue, Yiying, A comparative study of cellulose I and II and fibers and nanocrystals, Louisiana State University, LSU Digital Commons, LSU Master's Theses, Graduate School, 2011, 74 pgs.

* cited by examiner

*Primary Examiner* — Jonathan S Lau
(74) *Attorney, Agent, or Firm* — J. Clinton Wimbish; Maynard Nexsen PC (57) ABSTRACT

In one aspect, TEMPO-cellulose structures and method of making the same are described herein. Briefly, a method of synthesizing TEMPO-cellulose comprises disposing cellulose in an aqueous medium, disposing first and second oxidizing agents in the aqueous medium and oxidizing hydroxyl groups of the cellulose via the first and second oxidizing agents in the presence of a 2,2,6,6-tetramethylpiperidine 1-oxyl radical (TEMPO) catalyst.

10 Claims, 8 Drawing Sheets

Size-exclusion chromatography of TEMPO/NaOC1/oxone mediated cellulose

TEMPO-CELLULOSE STRUCTURES AND RELATED METHODS

RELATED APPLICATION DATA

The present invention claims priority pursuant to 35 U.S.C. § 119(e) to United States Provisional Patent Application Ser. No. 62/538,375 filed Jul. 28, 2017, which is incorporated herein by reference in its entirety.

STATEMENT OF GOVERNMENT RIGHTS

The claimed invention was made with U.S. Government support under grant number 1457888 awarded by the National Science Foundation (NSF). The government has certain rights in this invention.

BACKGROUND

Cellulose is a biologically renewable carbon reserve and the most bountiful polysaccharide on earth. Oxidation of the cellulose primary hydroxyl groups to carboxylate groups is a decisive reaction in cellulose chemistry, and plays an important role as a surface chemical modification of cellulose, affording materials with a variety of commercially useful properties.

TEMPO (2,2,6,6-tetramethylpiperidine 1-oxyl radical) catalysts can be used in oxidation reactions that form cellulose derivatives having carboxylate groups. Such derivatives, referred to as "TEMPO-cellulose" or "TEMPO-oxidized cellulose", are of particular interest because of their wide ranging applicability to various technologies. The complete biodegradable nature of oxidized cellulose under physiological conditions renders it beneficial in agricultural, cosmetic, and pharmaceutical applications. Oxidized cellulose is also being used for the treatment of hemorrhages during medical procedures and in the preparation of cellulosic products, such as wash-and-wear shirts, filter papers, tissue paper, and paper towels.

Currently, using TEMPO with NaBr- and NaClO-mediated oxidation forms TEMPO-cellulose together with cellulose 6-carboxaldehyde as an intermediate. However, cellulose aldehyde groups are thermally unstable and cause tinting of the oxidized cellulose product when it is heated or dried at temperatures greater than about 80° C. Moreover, undesirable cellulose aldehyde impurities can undergo hemiacetal linkages between cellulose fibrils.

The demand for environmentally friendly materials is ever increasing as combating global warming is becoming a priority for consumers and manufacturers. Because of its biodegradable nature, TEMPO-cellulose is well suited for use in the packaging and biodegradable plastics industries.

Accordingly, a need exists for improved TEMPO-cellulose structures and methods of making and using the same.

DETAILED DESCRIPTION

The subject matter set forth herein relates to TEMPO-cellulose structures and methods of making and using the same. The structures and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the instant disclosure.

In the present invention, cellulose microstructures (e.g., films, membranes) and nanostructures (e.g., nanofilms, nanomembranes, etc.) are prepared from the combination of TEMPO-oxidized cellulose form-I and form-II via different methods, including casting through filtration and a wet casting method. The cellulosic products set forth herein are polymeric products finding applicability and use in in the manufacture of alternative, intelligent packaging materials and other technical fields. The TEMPO-cellulose structures described herein exhibit improved physical and chemical properties compared to existing materials, and are biodegradable. Such structures are hydrophilic, have low contact angles, and are suitable replacements for existing polyethylene, polyvinylided, polyester, polyamide, or cellophane based structures commonly used in the packaging industry. Alternatively, hydrophobic surfaces having high contact angles are also contemplated for suitability in various applications, where desired.

I. Methods of Synthesizing TEMPO-Cellulose

In one aspect, a method of synthesizing TEMPO-cellulose is disclosed. The method comprises, disposing cellulose in an aqueous medium, disposing a first oxidizing agent and a second oxidizing agent in the aqueous medium, and oxidizing hydroxyl groups of the cellulose via the first and second oxidizing agents in the presence of a 2,2,6,6-tetramethylpiperidine 1-oxyl radical (TEMPO) catalyst. Notably, oxidizing the cellulose in the presence of multiple oxidizing reagents and a TEMPO catalyst obviates and prevents aldehyde side products and de-polymerization of cellulose chains typically caused by β-elimination.

In some embodiments, the first oxidizing agent comprises sodium hypochlorite (NaOCl) and the second oxidizing agent comprises oxone ($KHSO_5$). Other oxidizing agents may be used as alternatives to oxone, such agents include, for example and without limitation, potassium persulfate ($K_2S_2O_8$), sodium persulfate ($Na_2S_2O_8$), ammonium persulfate (($NH_4$)$_2S_2O_8$), sodium peroxide ($Na_2O_2$), calcium peroxide ($CaO_2$), lithium peroxide ($Li_2O_2$), barium peroxide ($BaO_2$), nickel peroxide ($Ni_2O_3$), nickel (II) peroxide hydrate ($NiO_2$ x$H_2O$), sodium perborate tetrahydrate ($NaBO_3$ 4$H_2O$), magnesium peroxide ($MgO_2$), terbium peroxide (TbO$_2$), sodium percarbonate (Na$_2$CO$_3$ 1.5 H$_2$O) and hydrogen peroxide (H$_2$O$_2$), and zinc peroxide (ZnO$_2$).

The aqueous medium can comprise an aqueous NaHCO$_3$ solution, a sodium phosphate buffer solution, or a sodium bicarbonate solution having a pH of between 6 and 10. Specific pH values are further discussed in the non-limiting examples set forth further below. The oxone with TEMPO and NaOCl are between 40 to 90% of the cellulose weight and the aqueous medium solution ranges from 10 to 100 volumes.

During cellulose oxidation, the reaction medium can be heated via conventional heating elements (e.g., heating mantles, plates, baths, etc.) or microwave irradiation. Where heated via heating elements, the reaction temperatures are from about 250° C. to 900° C. and pHs range from 7 to 10. Where microwave irradiation is used, the solution is heated from 40° C. to 100° C. and pHs range from 7 to 10. Conventional reaction times range from 4-30 hours and microwave irradiation times range from 10-60 minutes.

Notably, the present subject matter is improved over previously reported TEMPO-cellulose. For example, two different forms of TEMPO oxidized cellulose are synthesized (i.e., form-I and form-II) for the formation of cellulose membranes, nanomembranes, films, and/or nanofilms from the combination of TEMPO-oxidized cellulose form-I and form-II. Oxone (also known as potassium peroxymonosulfate (KHSO$_5$), MPS, potassium monopersulfate), which can optionally be used as an oxidizing agent in the reactions described herein, is a versatile agent that converts aldehydes to carboxylic acids. Oxone further exhibits many desirable chemical and physical properties. For example, oxone is highly stable, easily transportable, nontoxic to humans and the environment, has nonpolluting side products, and is cost-effective.

In certain embodiments, the cellulose C-6 carboxylates and their sodium salts are synthesized via a combination of TEMPO, NaOCl, and oxone in an aqueous solution (e.g., aqueous NaHCO$_3$ solution, sodium phosphate buffer, etc.) and pH 7.0-8.5. The two different forms of TEMPO-oxidized cellulose (i.e., form-I and form-II) are synthesized in one pot, and can be individually isolated from the solution and used in combination to form various cellulose structures. The TEMPO-oxidized cellulose form-I is a water insoluble form of cellulose, and TEMPO-oxidized cellulose form-II is a water-soluble form of cellulose. Cellulose nanofilms can be prepared using the combined TEMPO-oxidized cellulose form-I and form-II via two different methods, such as casting through filtration and wet casting methods.

Notably, the methods set forth herein provide oxidized cellulose free from any cellulose aldehyde impurities via shorter reaction times under microwave irradiation conditions to produce the cellulose carboxylates. In some embodiments, oxidative methods described herein can be applied to cellulose derivatives and/or other polysaccharides including, but not limited to, polysaccharides can be selected from the group consisting of one or more hemicelluloses, amylose, amylopectin or mixtures thereof.

II. TEMPO-Cellulose Structures

In further aspects, TEMPO-cellulose structures are provided. Such structures comprise a combination of cellulose form-I and cellulose form-II. The contact angle of water on a surface of the cellulose structure is 20 degrees or more, thus providing a hydrophilic surface and structure without having to coat or further surface treat the structure. The cellulose structures described herein can comprise contact angles of water on the surfaces thereof that are greater than 90 degrees.

In some instances, the cellulose structures described herein comprise a greater weight percent of cellulose form-I. In other instances, the cellulose structures described herein comprise a greater weight percent of cellulose form-II. The weight ratios of cellulose form-I and cellulose form-I in a structure range from 0 to 100%

A novel environmentally friendly method using stoichiometric amounts of oxone and catalytic amounts of TEMPO/NaOCl form the cellulose structures described herein. Such TEMPO-cellulose structures form products comprising combinations of cellulose form-I and cellulose form-II, which are useful in the development of cellulose nanofilms via two different methods, casting through filtration, and the wet casting method. In some embodiments, structure and products comprise cellulose derivative and/or other polysaccharide structures oxidized according to method described herein. Oxidized polysaccharide structures, for example, can be derived from one or more hemicelluloses, amylose, amylopectin or mixtures thereof.

Some non-limiting examples regarding the instant subject matter are provided below. Numerous modifications and adaptations will be readily apparent to those of skill in the art without departing from the instant disclosure.

Example 1

TEMPO/NaOCl/Oxone-Mediated Oxidation of Cellulose

Figure 1:
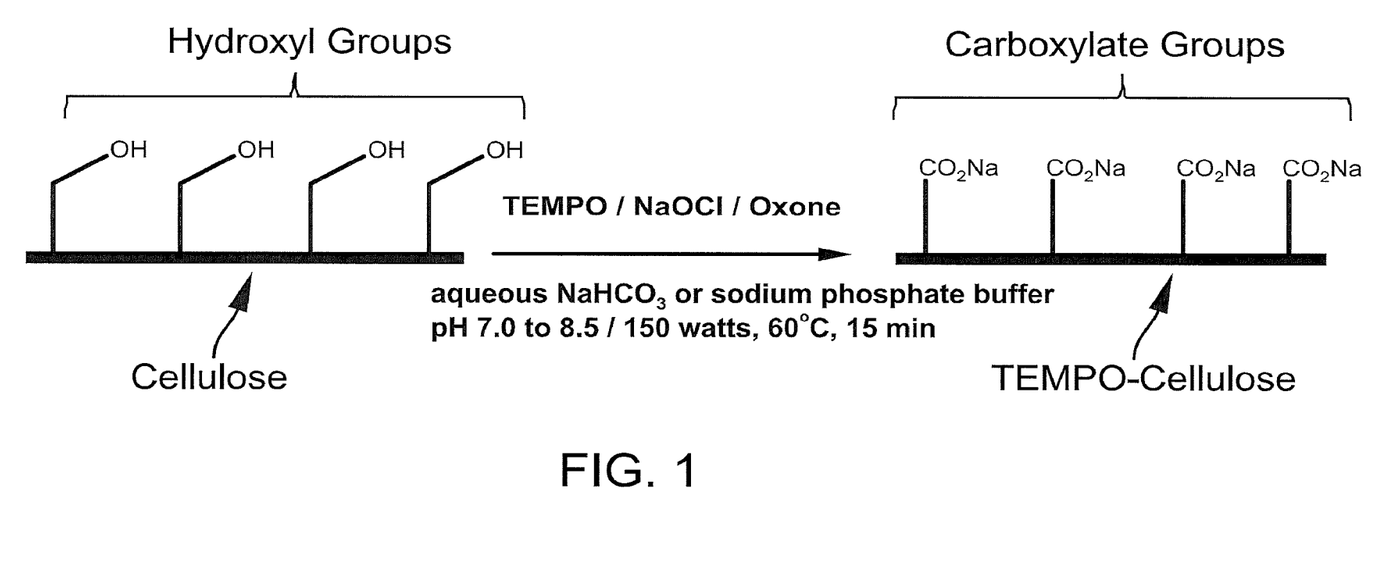
FIG. 1 is a schematic diagram of synthesizing TEMPO-cellulose according to an embodiment of the subject matter herein.
Figure 2:
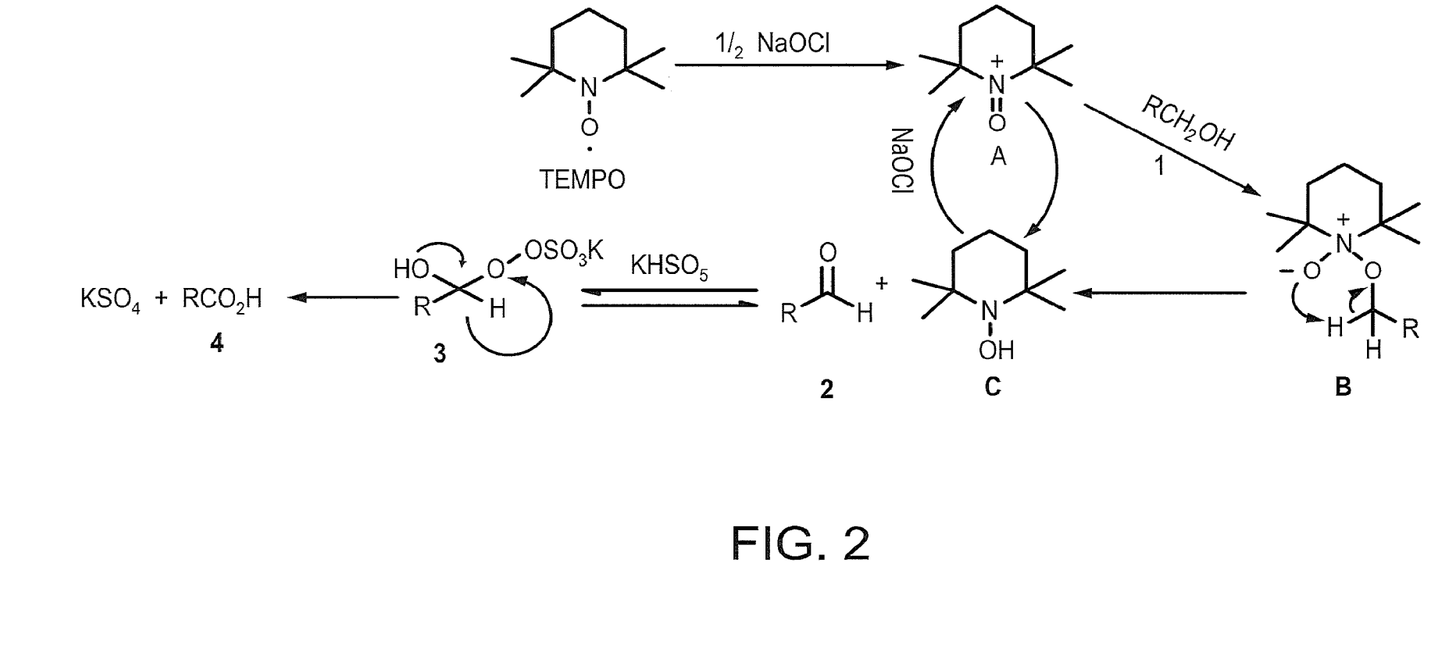
FIG. 2 is a schematic diagram of a chemical reaction for synthesizing TEMPO-cellulose according to an embodiment of the subject matter herein.

FIG. 1 is a schematic diagram of TEMPO/NaOCl/oxone-mediated oxidation of cellulose surface C6-OH groups via microwave irradiation. FIG. 2 is a schematic diagram of the mechanism for TEMPO/NaOCl/oxone-mediated oxidation of cellulose. Oxidation of cellulose can be carried out using TEMPO and NaOCl in combination with oxone in an aqueous NaHCO$_3$ solution at pH 7.0 to 8.5 under microwave irradiation conditions over 15 minutes, resulting in the formation of two different forms of TEMPO-oxidized cellulose, i.e. form-I and form-II. TEMPO-cellulose form-I (insoluble form) can be isolated by filtration of the reaction mixture from the above reaction. TEMPO-cellulose form-II is isolated from the filtrate by adding ethanol. No aldehyde groups were detected in the oxidized products and the de-polymerization of cellulose chains caused by β-elimination was advantageously avoided.

As an alternate to microwave irradiation, the cellulose oxidation can be carried out using TEMPO and NaOCl in combination with oxone in aqueous NaHCO$_3$ solution at pH 7.5 to 8.5 by conventional heating utilizing a heating mantel for 16 hours to synthesize TEMPO-oxidized cellulose form-I and form-II.

The cellulose oxidation can also be carried out using TEMPO and NaOCl in combination with oxone in 0.05M sodium phosphate buffer solution at pH 6.8 to 7.5 by conventional heating for 4-30 hours, to synthesize TEMPO-oxidized cellulose form I and form II.

Additionally, the oxidation of cellulose can be carried out via combining oxone (KHSO$_5$), and/or related reagents, with TEMPO and NaOCl from 40-90% of cellulose weight and sodium bicarbonate solution ranging from 10 to 100 volumes.

In some cases, oxidation of cellulose is carried out using TEMPO/NaOCl in combination with oxidizing agents selected from oxone (KHSO$_5$), K$_2$S$_2$O$_8$ (potassium persulfate), Na$_2$S$_2$O$_8$ (sodium persulfate), (NH$_4$)$_2$S$_2$O$_8$ (ammonium persulfate), Na$_2$O$_2$ (sodium peroxide), CaO$_2$ (calcium peroxide), Li$_2$O$_2$ (lithium peroxide) BaO$_2$ (barium peroxide), Ni$_2$O$_3$ (nickel peroxide), NiO$_2$ xH$_2$O nickel (II) (peroxide hydrate), NaBO$_3$ 4H$_2$O (sodium perborate tetrahydrate), MgO$_2$ (magnesium peroxide complex), TbO$_2$ (terbium peroxide), Na$_2$CO$_3$ 1.5 H$_2$O (sodium percarbonate) H$_2$O$_2$ (30%) (hydrogen peroxide), ZnO$_2$ (zinc peroxide). The bicarbonate solutions selected from the bicarbonate salts of Na, K, Rb, and Cs.

Reaction temperatures range between about 250° C. and 900° C. and pHs range from 7 to 10 in combination with oxone (KHSO$_5$; 40 to 90% of cellulose weight) and TEMPO/NaOCl. Where microwave irradiation is employed, the irradiation temperatures range from about 400° C. to about 100° C. and pHs from 7 to 10 in combination with oxone (KHSO$_5$; 40 to 90% of cellulose weight) and TEMPO/NaOCl. The preparation and isolation of TEMPO-cellulose form-I and form-II by using the combination of oxone (KHSO$_5$) with TEMPO and NaOCl in bicarbonate aqueous solutions at pH>7 to 10.

The precipitation of cellulose form-II from the reaction mass filtrate via alcohols comprises alcohols including but not limited to methanol, ethanol, isopropanol, butanol, isobutanol, etc., and alcohols having a carbon count, number, or quantity ranging from C1 to C10.

The oxidation of cellulose with oxone (KHSO$_5$) in combination with TEMPO/NaOCl, has reaction times ranging from 4 to 30 hours and microwave irradiation times range from 10 to 60 minutes. The oxidation of cellulose with oxone (KHSO$_5$) in combination with TEMPO/NaOCl, the isolated TEMPO-cellulose has form-I as a water insoluble product and TEMPO-cellulose form-II as a water-soluble product.

Combining TEMPO-cellulose form-I and TEMPO cellulose form-II in weight ratios ranging from 0 to 100% provide a material having a minimum contact angle of about 20 degrees thus providing a super hydrophilic surface. Notably, the TEMPO-cellulose structures and methods provided herein form strong, modifiable, barrier material that maintain the crystalline structure of cellulose, almost identical to the biologically inert plants from which cellulose is derived.

Example 2

Characterization of TEMPO-Cellulose

Figure 3:
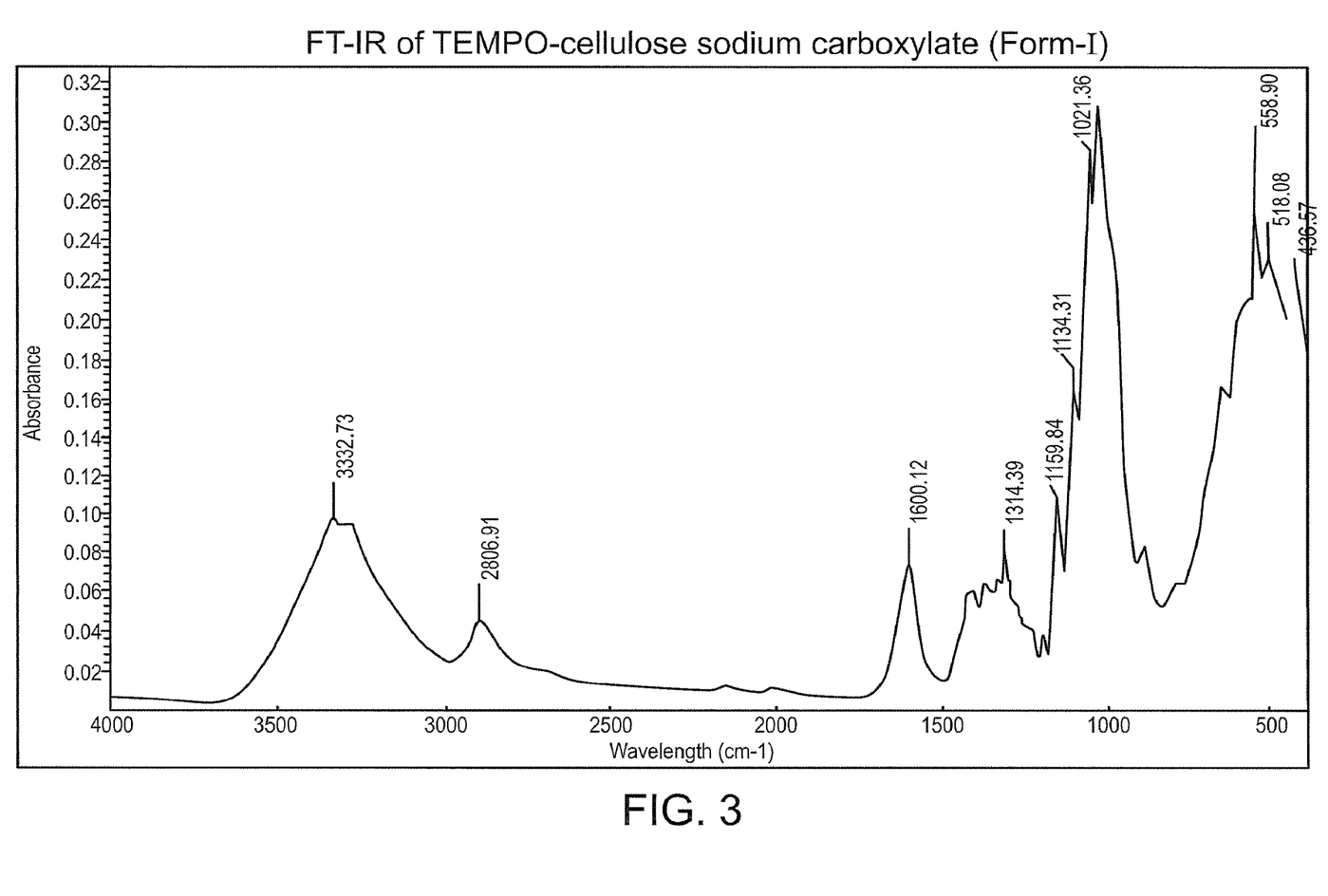
FIGS. 3 and 4 are Fourier Transform Infrared (FTIR) spectra for TEMPO-cellulose structures according to embodiments of the subject matter herein.
Figure 4:
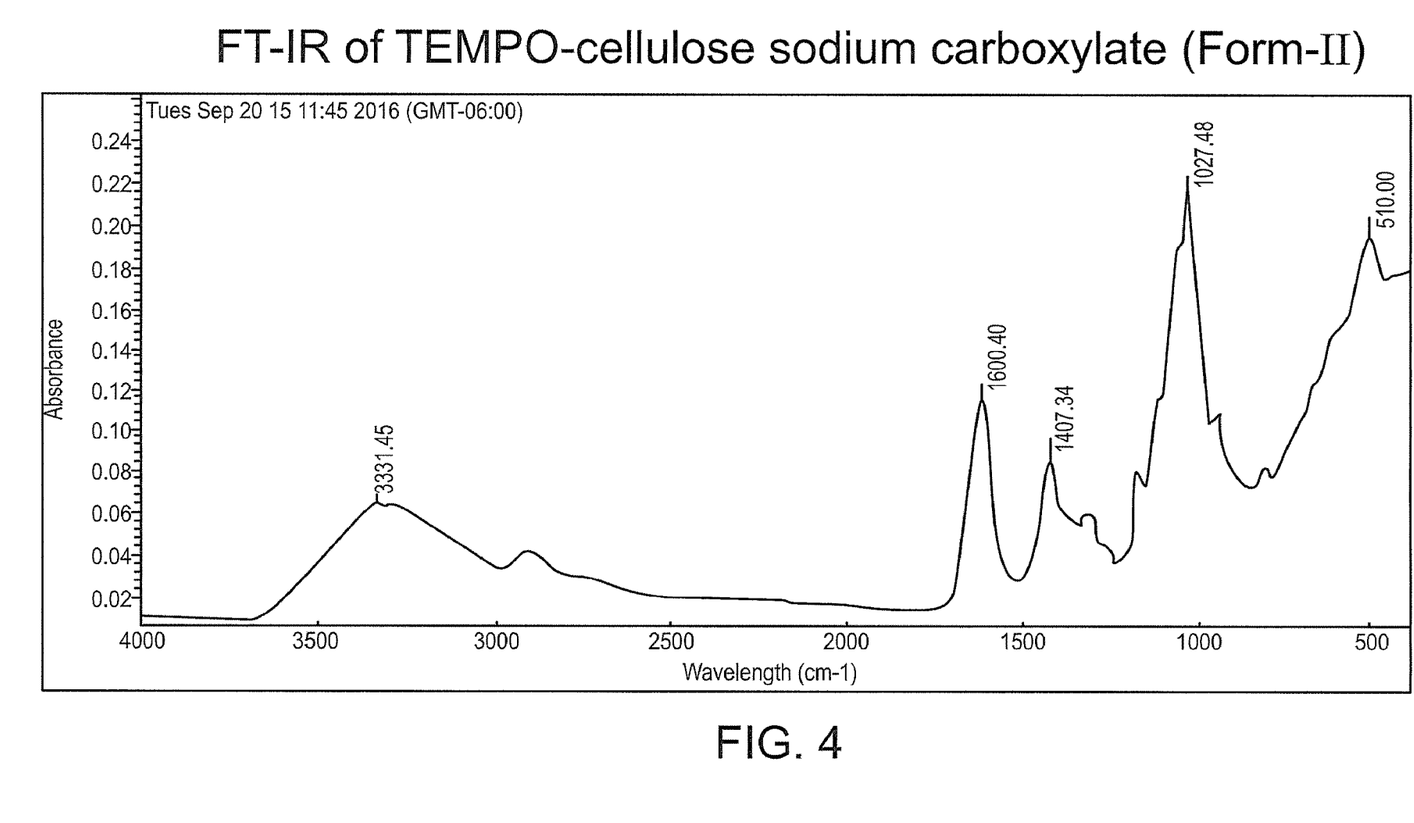
Figure 5:
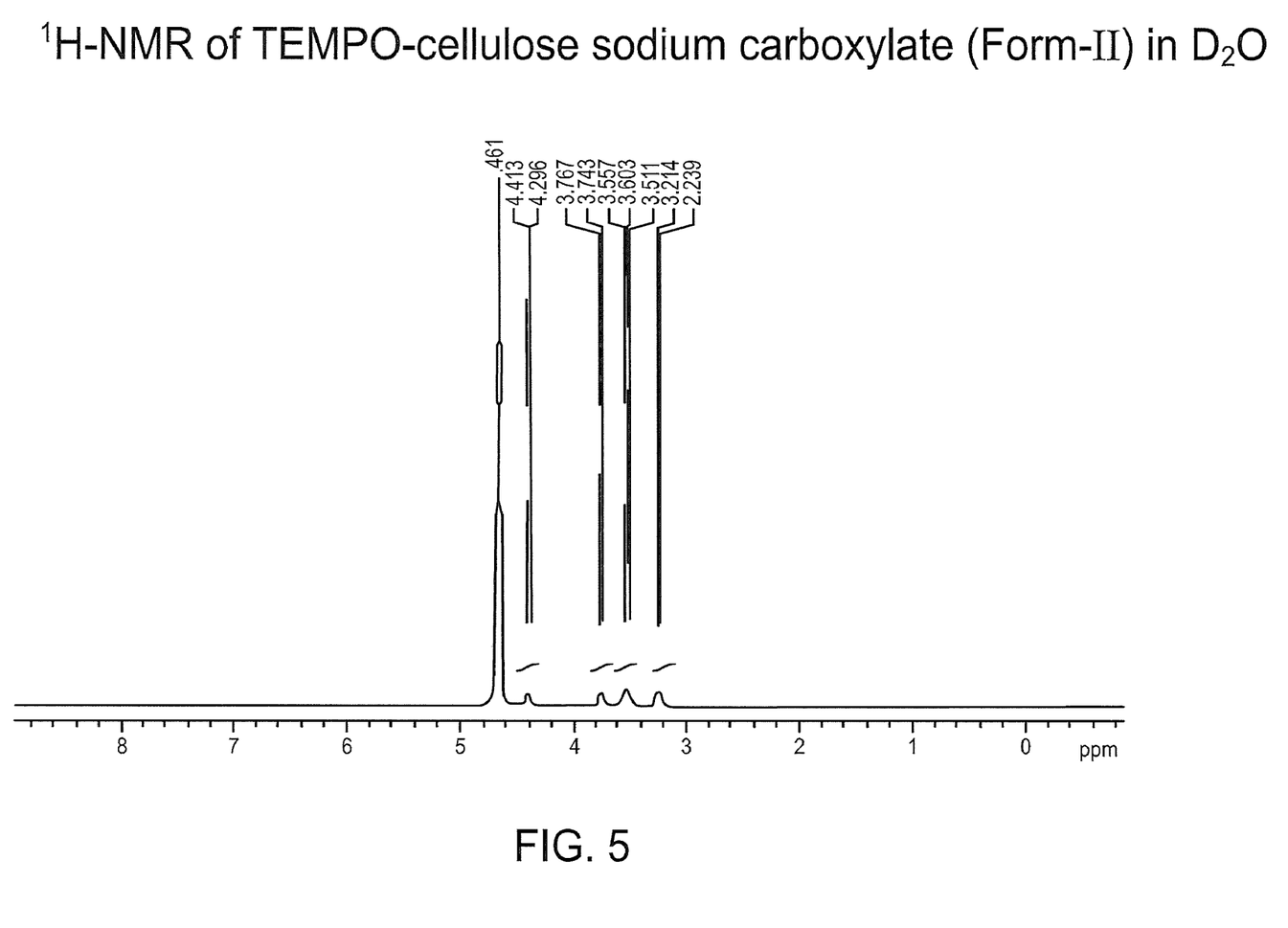
FIGS. 5 and 6 are Nuclear Magnetic Resonance (NMR) spectra for TEMPO-cellulose structures according to embodiments of the subject matter herein.
Figure 6:
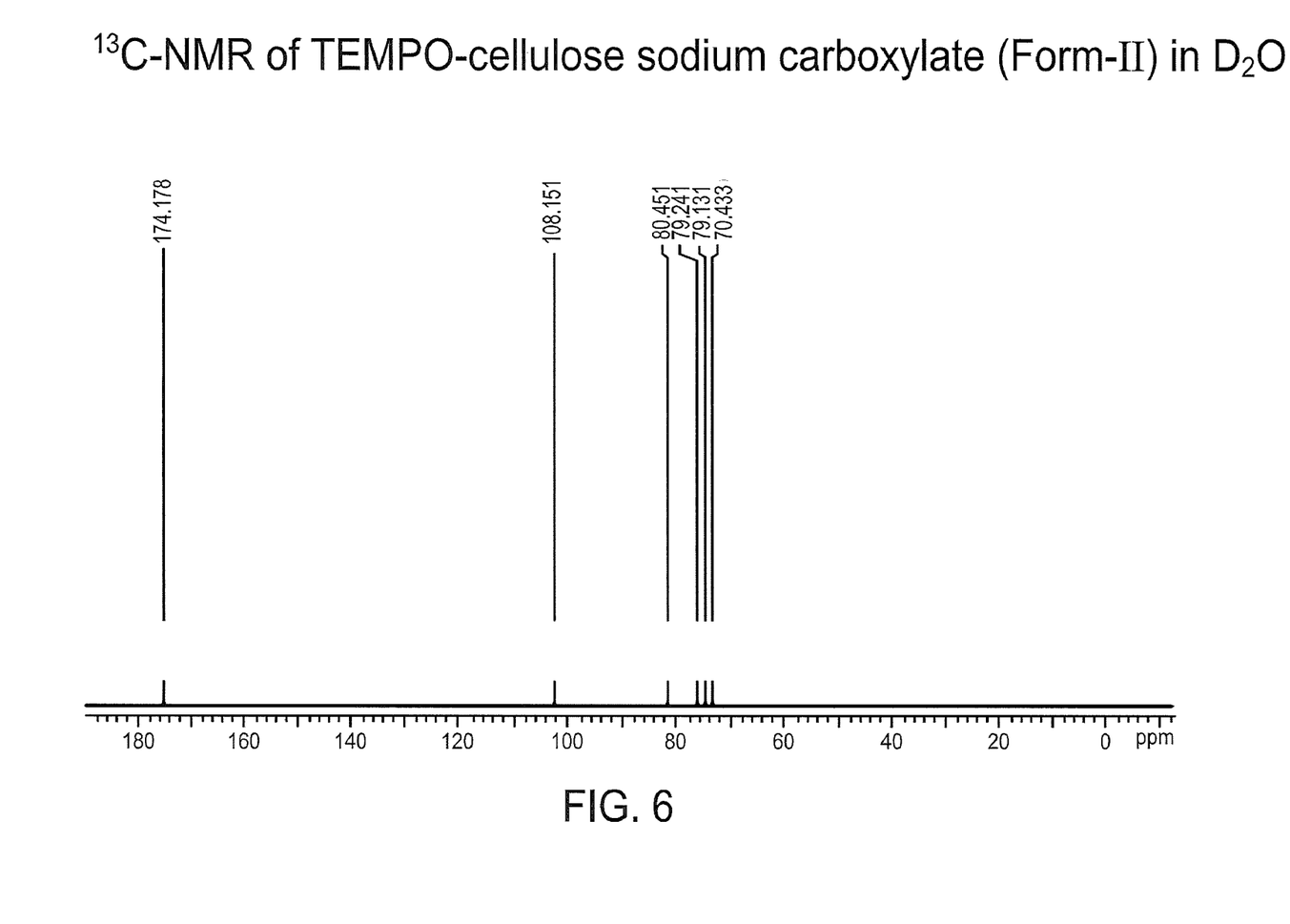

FIG. 3 is the Fourier transform infrared (FTIR) spectroscopy spectra for TEMPO-cellulose sodium carboxylate, form-I. FIG. 4 is the FTIR spectra for TEMPO-cellulose sodium carboxylate, form-II. FIG. 5 is Hydrogen-Nuclear Magnetic Resonance (H-NMR) spectra of Tempo-cellulose form-II. FIG. 6 is Carbon 13-NMR spectra of Tempo-cellulose form-II.

Figure 7:
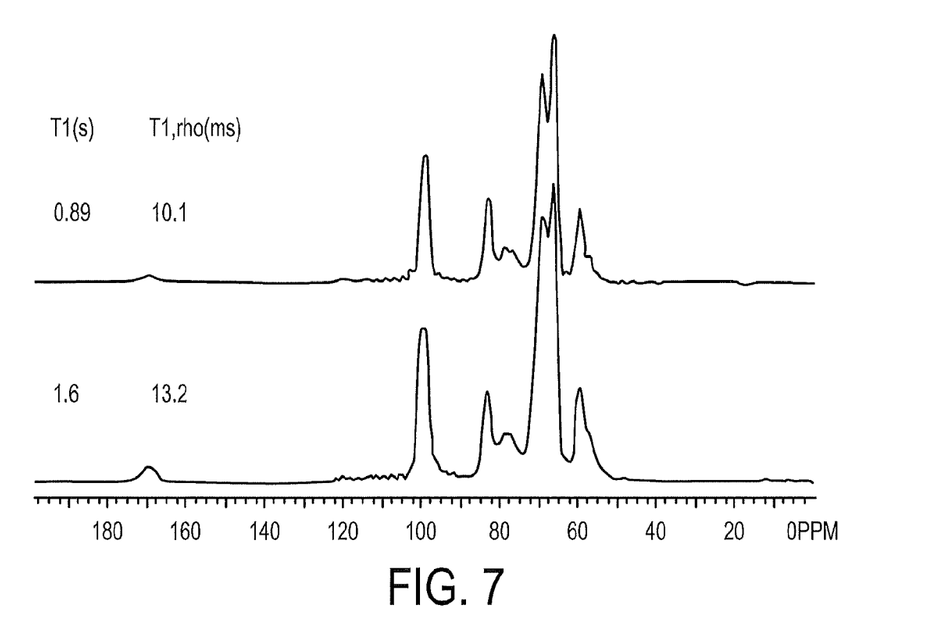
FIG. 7 is NMR spectra for TEMPO-cellulose form-I and form-II for TEMPO-cellulose structures according to embodiments of the subject matter herein.

FIG. 7 is the solid state NMR spectra of TEMPO-cellulose sodium carboxylate form-I, which shows a small carbonyl peak at ~170 ppm indicating the presence of the carboxylate group. In form-II, the same peak is observed but is much greater in area, indicating a greater amount of oxidation of primary hydroxyl group to carboxylate. The presence of less carboxyl resonance in the spectrum of TEMPO-cellulose sodium carboxylate form-I is consistent with the poor water solubility of this TEMPO-cellulose form.

From the solid state NMR data, it is further apparent that TEMPO-cellulose sodium carboxylate form-II shows a broader carbonyl peak at 170 ppm, indicating a greater amount of carboxylate functionalities in form-II compared to form-I. The presence of more carboxylate groups in TEMPO-cellulose sodium carboxylate form-II is the reason for its greater solubility in water.

Figure 8:
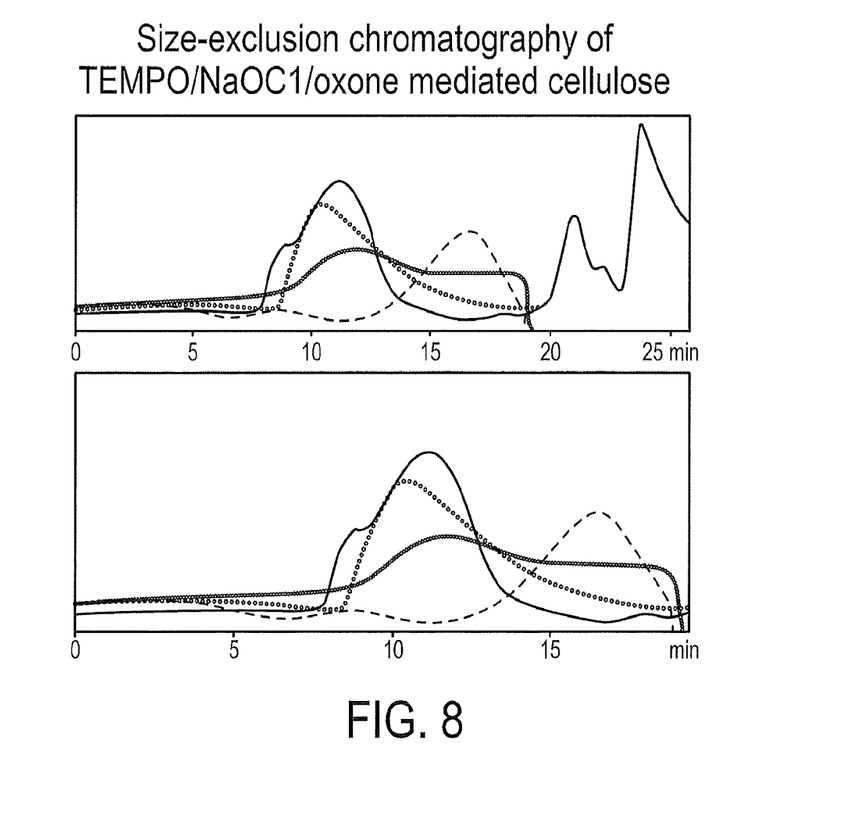
FIG. 8 is size-exclusion chromatography II for TEMPO-cellulose structures according to embodiments of the subject matter herein.

FIG. 8 is molecular mass determination of TEMPO-cellulose form-II. In order to estimate the molecular weight of the peak eluting at approximately 11.2 minutes (in FIG. 8) molecular weight dextran standards (10 KDa, 5 KDa, 1 KDa and 180 Da, Sigma) were run in sequence with the sample. A calibration curve was constructed by plotting the log of the molecular weight and the elution volume of the standards. This curve was then used to estimate the molecular weight of the sample (TEMPO-cellulose sodium carboxylate Form-II) to be approximately 7.5 KDa.

Figure 9:
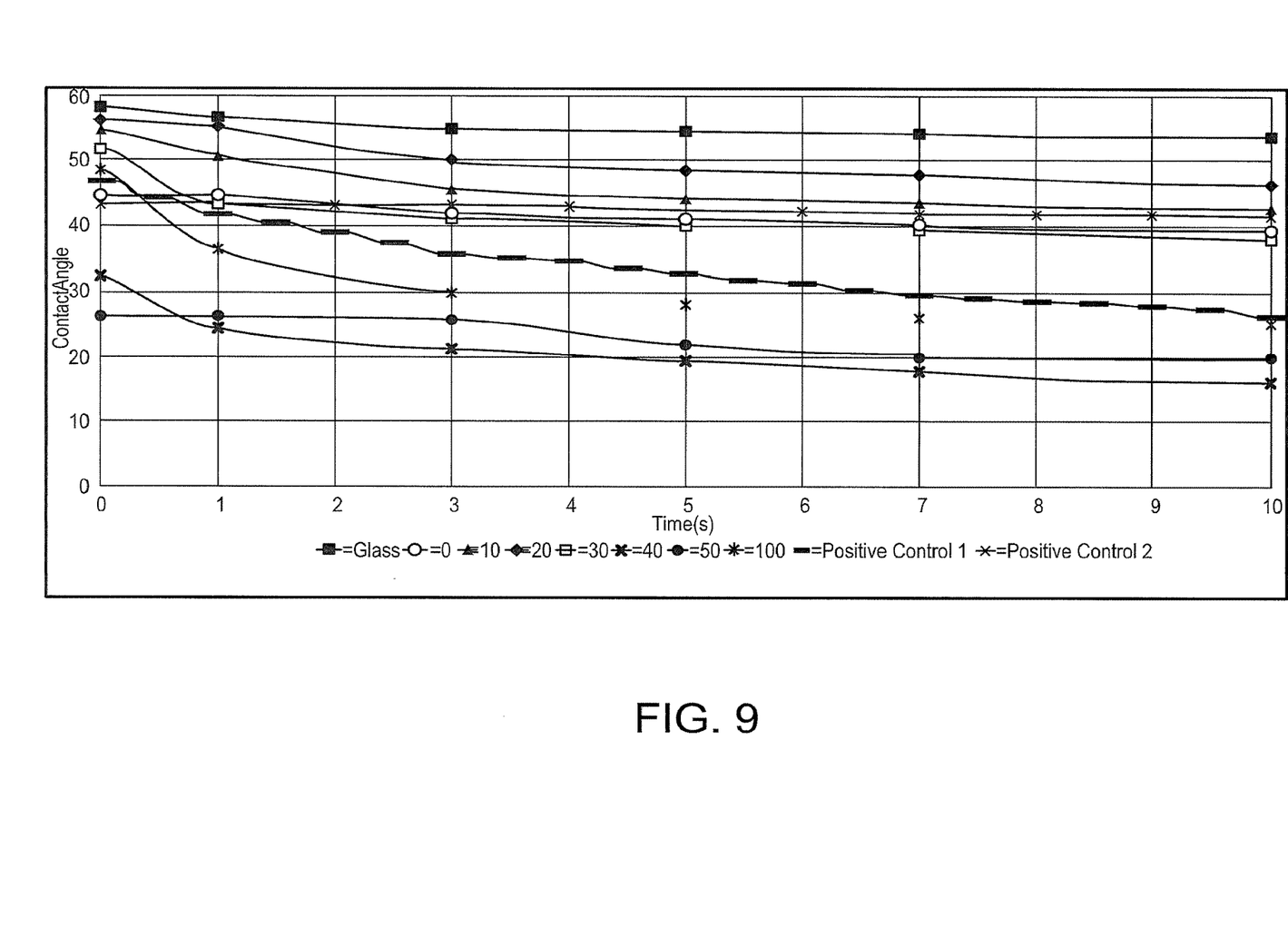
FIG. 9 depicts contact angle measurements for TEMPO-cellulose structures with varying percent of water soluble material according to embodiments of the subject matter herein.

FIG. 9 is the contact angle measurements of fractionalized TEMPO-oxidized cellulosic materials varying the percent water soluble material.

The methods and structures described herein can be used to provide structures having many technical benefits, including but not limited to biodegradable packaging materials, commercial packaging materials, supports or backings for cell growth, medical dressings, clothing, additives for membrane synthesis, gas barrier membranes, and other commercial products having biodegradable aspects.

It will be understood that various details of the subject matter described herein may be changed without departing from the scope of the subject matter described herein. Furthermore, the foregoing description is for the purpose of illustration only, and not for the purpose of limitation.

The invention claimed is:

1. A method of synthesizing TEMPO-cellulose, the method comprising:
    disposing cellulose in an aqueous medium;
    disposing a first oxidizing agent and a second oxidizing agent in the aqueous medium, wherein the first oxidizing agent comprises sodium hypochlorite (NaOCl) and the second oxidizing agent comprises oxone (KHSO$_5$); and
    oxidizing hydroxyl groups of the cellulose via the first and second oxidizing agents in the presence of a 2,2,6,6-tetramethylpiperidine 1-oxyl radical (TEMPO) catalyst, wherein the TEMPO-cellulose comprises a mixture of cellulose form-I and cellulose form-II.

2. The method of claim 1, wherein the aqueous medium is an aqueous NaHCO3 solution, a sodium phosphate buffer solution, or a sodium bicarbonate solution.

3. The method of claim 1, wherein the pH of the aqueous medium is between 6 and 10.

4. The method of claim 1 further comprising heating the aqueous medium while oxidizing the cellulose.

5. The method of claim 4, wherein heating the aqueous medium comprises exposing the aqueous medium to microwave irradiation.

6. The method of claim 1, wherein the TEMPO-cellulose is formed as a film or membrane.

7. The method of claim 6, wherein the film or membrane has a contact angle is 20 degrees or more.

8. The method of claim 1, wherein the TEMPO-cellulose is hydrophilic.

9. The method of claim 1, wherein the TEMPO-cellulose is free from cellulose aldehyde impurities.

10. The method of claim 1, wherein the first oxidizing agent and the second oxidizing agent are concurrently disposed in the aqueous medium having cellulose disposed therein.

* * * * *